United States Patent [19]

Macor

[11] Patent Number: 5,169,947
[45] Date of Patent: * Dec. 8, 1992

[54] 3-(1,2,5,6-TETRAHYDROPYRIDYL)-PYRROLOPYRIDINES

[75] Inventor: John E. Macor, Mystic, Conn.

[73] Assignee: Pfizer Inc., New York, N.Y.

[*] Notice: The portion of the term of this patent subsequent to Sep. 24, 2008 has been disclaimed.

[21] Appl. No.: 763,081

[22] Filed: Sep. 20, 1991

Related U.S. Application Data

[63] Continuation of Ser. No. 576,429; filed as PCT/US89/00231, Jun. 23, 1989, Pat. No. 5,051,412.

[51] Int. Cl.$^5$ .................................. C07D 471/04
[52] U.S. Cl. ........................................ 546/113
[58] Field of Search ............................. 546/113

[56] References Cited

U.S. PATENT DOCUMENTS

| | | | |
|---|---|---|---|
| 3,993,764 | 11/1976 | Dumont et al. | 424/267 |
| 4,196,209 | 4/1980 | Dumont et al. | 424/267 |
| 4,232,031 | 11/1980 | Dumont et al. | 546/273 |
| 4,278,677 | 7/1981 | Nedelec et al. | 546/273 |
| 5,051,412 | 9/1991 | Macor | 546/113 |

OTHER PUBLICATIONS

Kennet et al., *Eur. Jl. of Pharmacology*, 141, 429-35 (1987).
Freter, K., *J. Org. Chem.*, 40, 2525-9 (1975).
Bendotti et al., *Life Sciences*, 41, 635-42 (1987).
Hutson et al., *Psychopharmacology*, 95, 550-52 (1988).

*Primary Examiner*—Bernard Dentz
*Attorney, Agent, or Firm*—Peter C. Richardson; Paul H. Ginsburg; Seymour G. Bekelnitzky

[57] ABSTRACT

Compounds of the formula

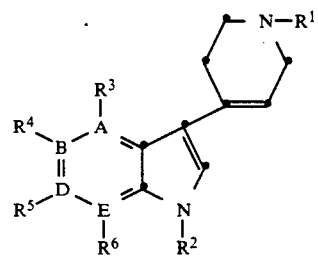

wherein one of A, B, D and E is N and the remaining three atoms are C; $R^1$ and $R^2$ are independently selected from hydrogen and $C_1$ to $C_6$ alkyl; and $R^3$, $R^4$, $R^5$ and $R^6$ are independently selected from hydrogen, halogen, hydroxy, $C_1$-$C_6$ alkyl, $C_1$-$C_8$ alkoxy, phenyl-$C_1$-$C_6$ alkoxy, phenoxy, —$NR^7R^8$ wherein $R^7$ and $R^8$ are independently selected from hydrogen, $C_1$-$C_6$ alkyl, $C_1$-$C_6$ alkanoyl, and $COOR^9$ wherein $R^9$ is hydrogen or $C_1$-$C_6$ alkyl, cyano, $COOR^{10}$ wherein $R^{10}$ is hydrogen or $C_1$-$C_6$ alkyl, and $CONR^{11}R^{12}$ where $R^{11}$ and $R^{12}$ are independently selected from hydrogen and $C_1$-$C_6$ alkyl, and the pharmaceutically acceptable salts thereof. The compounds are useful psychotherapeutics and may be used in treating obesity, depression and disorders wherein aggression is a symptom.

2 Claims, No Drawings

3-(1,2,5,6-TETRAHYDROPYRIDYL)-PYRROLOPYRIDINES

This is a continuation of application Ser. No. 07/576,429, filed on Sep. 17,1990, now U.S. Pat. No. 5,051,412, which claims priority from PCT patent application PCT/U.S. No. 89/00231, filed Jun. 23, 1989.

BACKGROUND OF THE INVENTION

The present invention relates to certain pyrrolopyridines, methods of preparing such compounds, pharmaceutical compositions comprising such compounds, and the use of such compounds in treating obesity, depression, and disorders wherein aggression is a symptom (e.g., schizophrenia).

U.S. Pat. Nos. 4,232,031 and 4,278,677 refer to tetrahydropyridylindoles having antidepressive, antiemetic, antiparkinsonian and neuroleptic activity.

U.S. Pat. Nos. 3,993,764 and 4,196,209 refer to piperidylindoles having antidepressant, antiemetic and antiparkinsonian activity.

J. Guillaume et al., *Eur. J. Med. Chem.*, 22, 33–43 (1987) refer to tetrahydropyridinylindoles having serotoninergic and anti-dopaminergic properties.

K. Freter, *J. Org. Chem.*, 40, 2,525–2,529 (1975), refers to the reaction of cyclic ketones and indoles to prepare 3-cycloalkenylindoles.

G. H. Kennet et al., *European Journal of Pharmacology*, 141, 429–435 (1987), C. Bendotti et al., *Life Sciences*, 41, 635–642 (1987), M. Carli et al., *Psychopharmacology*, 94, 359–364 (1988) and P. H. Hutson et al., *Psychopharmacology*, 95, 550–552 (1988), refer to the effects of RU 24969 (5-methoxy-3(1,2,3,6-tetrahydro-4-pyridinyl)-1H-indole) as a 5-hydroxytryptamine agonist, its potential anxiolytic, and antidepressant effects and its effects on feeding.

SUMMARY OF THE INVENTION

The present invention relates to compounds of the formula

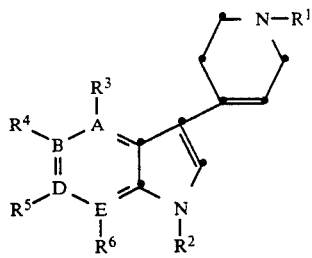

wherein one of A, B, D and E is N and the remaining three atoms are C;

$R^1$ and $R^2$ are independently selected from hydrogen and $C_1$ to $C_6$ alkyl; and $R^3$, $R^4$, $R^5$ and $R^6$ are independently selected from hydrogen, halogen, hydroxy, $C_1-C_6$ alkyl, $C_1-C_8$ alkoxy, phenyl-$C_1-C_6$ alkoxy, phenoxy, —$NR^7R^8$ wherein $R^7$ and $R^8$ are independently selected from hydrogen, $C_1-C_6$ alkyl, $C_1-C_6$ alkanoyl, and $COOR^9$ wherein $R^9$ is hydrogen or $C_1-C_6$ alkyl, cyano, $COOR^{10}$ wherein $R^{10}$ is hydrogen or $C_1-C_6$ alkyl, and $CONR^{11}R^{12}$ where $R^{11}$ and $R^{12}$ are independently selected from hydrogen and $C_1-C_6$ alkyl, and the pharmaceutically acceptable salts thereof.

The pyrrolo[3,2-b]pyridines of the formula I wherein $R^1$, $R^2$, $R^5$ and $R^6$ are hydrogen, $R^3$ is absent, $R^4$ is as defined above, A is N, and B, D and E are C are preferred. Particularly preferred compounds are the foregoing compounds wherein $R^4$ is hydrogen, $C_1-C_6$ alkoxy (e.g., methoxy) or hydroxy.

Unless otherwise indicated, the alkyl groups referred to herein, as well as the alkyl moieties of other groups referred to herein (e.g., alkoxy and alkanoyl), may be linear or branched. They may also be cyclic or be linear or branched and contain cyclic moieties.

DETAILED DESCRIPTION OF THE INVENTION

The compounds of the formula I are prepared by reacting a compound of the formula

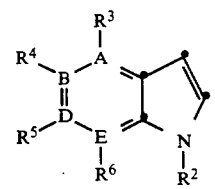

wherein A, B, D, E, $R^2$, $R^3$, $R^4$, $R^5$ and $R^6$ are as defined above, with a piperidone monohydrate hydrohalide (preferably, the hydrochloride) in the presence of a base. Suitable bases include sodium or potassium alkoxides and alkylmagnesium halides. A preferred base is sodium methoxide. The solvent should be an inert solvent. Suitable solvents include alcohols, dimethylformamide, and tetrahydrofuran. The preferred solvent is methanol. The reaction is conducted at a temperature of about 60° to about 120° C., preferably about 65° to about 70° C., most preferably at the reflux temperature of the solvent. The pressure is not critical. Generally, the reaction will be conducted at a pressure of about 0.5 to about 2 atmospheres, preferably at ambient pressure (about 1 atmosphere).

Compounds of the formula I may be converted into the salt of an inorganic or organic acid, preferably into a pharmaceutically acceptable salt, by reacting substantially stoichiometric amounts of the base and the acid. Examples of such salts are hydrochlorides, hydrobromides, nitrates, sulfates, phosphates, acetates, oxalates, maleates, fumarates, tartrates, lactates, malates, malonates, citrates, salicylates, methanesulfonates, benzenesulfonates, toluenesulfonates and naphthalenesulfonates.

These or other salts of the new compounds, such as, for example, picrates, can also be used to purify the free bases obtained, by converting the free base into a salt, separating the salt and if appropriate recrystallizing it or purifying it by another means, and liberating the base again from the salt.

Compounds of the formula II wherein $R^2$, $R^5$ and $R^6$ are hydrogen, $R^3$ is absent, $R^4$ is as defined above, A is N, and B, D and E are C are novel. Specific novel compounds are the following:

5-hydroxypyrrolo[3,2-b]pyridine;
5-dimethylaminopyrrolo[3,2-b]pyridine;
5-ethoxypyrrolo[3,2-b]pyridine;
5-propoxypyrrolo[3,2-b]pyridine;
5-butoxypyrrolo[3,2-b]pyridine;
5-isopropoxypyrrolo[3,2-b]pyridine;
5-t-butoxypyrrolo[3,2-b]pyridine;
5-benzyloxypyrrolo[3,2-b]pyridine;
5-cyclopentoxypyrrolo[3,2-b]pyridine; and 5-methylpyrrolo[3,2-b]pyridine.

The novel compounds of the formula II are prepared by reacting a compound of the formula

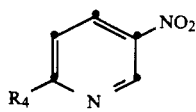

III wherein R⁴ is as defined above with 2-(4-chlorophenoxy)acetonitrile in the presence of a strong base in an appropriate polar solvent. (See Makosza, et. al. (*Liebigs Ann. Chem.*, 1988, 203)). Suitable bases include tertiary sodium or potassium alkoxides. The preferred base is potassium t-butoxide. Suitable solvents include tetrahydrofuran, diethyl ether, and dimethylformamide. The preferred solvent is tetrahydrofuran. The reaction is conducted at a temperature of about −78° C. to about 25° C., preferably at −10° C. The pressure is not critical. Generally, the reaction will be conducted at a pressure of about 0.5 to about 2 atmospheres, preferably at ambient pressure (about 1 atmosphere). The product of such reaction is purified by neutralization of the reaction mixture using a mineral acid, preferably dilute hydrochloric acid, and standard extractive isolation using ethyl acetate, diethyl ether, or methylene chloride, preferably diethyl ether. The organic residue from the extraction is reacted under a hydrogen atmosphere in a suitable solvent with a metal catalyst at a temperature between about 0° C. and about 70° C., most preferably at ambient temperature (about 20° C.). Suitable solvents include methanol, ethanol, propanol, ethyl acetate, dimethylformamide and acetic acid. Acetic acid is the preferred solvent. Suitable metal catalysts include mixtures of palladium on carbon, palladium oxide, and Raney nickel. The preferred catalyst is 10% palladium on carbon. The hydrogen pressure of the reaction should be maintained between about 1 atmosphere to about 5 atmospheres, preferably at about 3 atmospheres.

The present invention also relates to the use of compounds of the formula I and their pharmaceutically acceptable salts in the treatment and prevention of obesity, depression and disorders wherein aggression is a symptom. The effectiveness of such compounds may be measured by administering the compounds to mice and measuring weight loss. A compound of the formula I or a pharmaceutically acceptable salt thereof can be administered alone or in admixture with suitable excipients. Such a mixture may contain one or more compounds of the formula I or pharmaceutically acceptable salts thereof in an amount of about 0.1 to about 99.9%. A typical dose for an adult human would range from about 1 mg to about 500 mg. The exact dosage of a compound of the formula I or a pharmaceutically acceptable salt thereof will depend upon such factors as the age, weight and condition of the patient and the severity of disease. In general, however, a therapeutically effective dose of a compound of the formula I or a pharmaceutically acceptable salt thereof will range from about 0.1 to about 20 mg/kg body weight of the subject to be treated per day, preferably about 2 to about 10 mg/kg per day, taken in up to 4 divided doses.

Possible pharmaceutical formulations include all those formulations with which the expert is familiar, such as, for example, suppositories, powders, granules, tablets, capsules, dragees, suspensions and solutions for oral administration, injectable solutions and transdermal systems. Solid, semi-solid or liquid excipients or diluents can be used to prepare pharmaceutical formulations. These agents include binders, lubricants, emulsifiers and the like. Examples of such agents are: starch, such as potato starch and cereal starch, sugar, such as lactose, sucrose, glucose, mannitol and sorbitol, cellulose, such as crystalline cellulose, methylcellulose, calcium carboxymethylcellulose, sodium carboxymethyl cellulose and hydroxypropylcellulose, inorganic materials, such as potassium phosphate, calcium sulfate, calcium carbonate, talc, gelatin, gum arabic, polyvinylpyrrolidone, magnesium stearate, cacao butter, surface-active substances, such as fatty acid glycerides, fatty acid sorbitan esters, fatty acid esters of sucrose and polyglycerol, and others The following Examples illustrate the preparation of the compounds of the present invention. Melting points are uncorrected. NMR data are reported in parts per million ($f$) and are referenced to the deuterium lock signal from the sample solvent. The starting materials pyrrolo[3,2-b]pyridine (V. A. Azimov et al., *Khim. Geterotsikl Soedin.*, 10, 1,425 (1977)), pyrrolo[3,2-c]pyridine (J. R. Dormoy, et al. *Fr. Demande FR* 2,564,836 (Nov. 29, 1985)), pyrrolo[2,3-c]pyridine (A. A. Prokopov et al. *Khim. Geterotsikl Soedin.*, 8, 1,135 (1977)), pyrrolo[2,3-b]pyridine (Aldrich Chemical Co.), 5-methoxypyrrolo[3,2-b]pyridine (M. Makoska, et al., *Liebigs Ann Chem.*, 203 (1988)), and 4-methyl-5-nitro-1H-pyridine-2-one (H. E. Baumgarten, et al. *JACS*, 74, 3,828 (1952)) are commercially available or may be prepared according to published methods.

EXAMPLE 1

A. General procedure for the synthesis of 3-(1,2,5,6-tetrahydropyridyl)pyrrolopyridines; Compounds 1a–1m, 2, 3a, 3b, 3c and 4

To a stirred solution of Na (2.53 g, 110 mmol, 11 eq) in absolute methanol (50 ml) at room temperature was added the appropriate pyrrolopyridine (10.00 mmol) and piperidone monohydrate hydrochloride (4.60 g, 30.0 mmol, 3.0 eq). The resultant mixture was then heated at reflux under nitrogen for 2–24 hours depending on the substrate. The resultant reaction mixture was cooled, and concentrated hydrochloric acid (37%, 9.0 ml, 110 mmol) was added dropwise with vigorous stirring. The resultant mixture was then evaporated under reduced pressure, and the residual slurry placed in water (50 ml). This aqueous mixture was extracted with ethyl acetate (5×50 ml), and these extracts were combined, dried (Na₂SO₄), and evaporated under reduced pressure. The residue was either triturated directly or column chromatographed using silica gel (approximately 100 g) and elution with the appropriate solvent system yielding the desired 3-(1,2,5,6-tetrahydropyridyl)pyrrolopyridine, one of Compounds 1a–1m or compound 2, 3a, 3b, 3c or 4.

B. 3-(1,2,5,6-Tetrahydropyridyl)pyrrolo[3,2-b]pyridine (Compound 1a)

The reaction time was 4 hours. Flash chromatography of the extraction residue using silica gel (approximately 200 g) and elution with 5% triethylamine in methanol yielded Compound 1a (44%) as a pale yellow solid: mp, 198°–200° C.; IR (KBr) 3,220, 3,100–2,740, 1,650, 1,615, 1,550, 1,500, 1,460, 1,430, 1,260, 1,040 cm⁻¹; ¹H NMR (DMSO-d₆) δ 8.33 (dd, J=4.7 and 1.2 Hz, 1H), 7.72 (dd, J=8.3 and 0.8 Hz, 1H), 7.55 (s, 1H), 7.11 (br m, 1H), 7.09 (dd, J=8.3 and 4.7 Hz, 1H), 3.39

(d, J=2.6 Hz, 2H), 2.92 (t, J=5.8 Hz, 2H), 2.36 (br m, 2H); $^{13}$C NMR (DMSO-d$_6$) δ 143.6, 142.0, 129.5, 128.2, 125.0, 121.6, 118.4, 116.3, 116.0 44.8, 42.8, 27.2; LRMS (m/z, relative intensity) 200 (30), 199 (M+, 100), 198 (92), 170 (75), 169 (39), 155 (15), 131 (35); HRMS calculated for C$_{12}$H$_{13}$N$_3$:199.1110, found: 199.1096.

C.
5-Methoxy-3-(1,2,5,6-tetrahydropyridyl)pyrrolo[3,2-b]-pyridine (Compound 1b)

The reaction time was 6 hours. Flash chromatography of the extraction residue using silica gel (approximately 100 g) and elution with 10% triethylamine in methanol, followed by crystallization of the recovered oil (R$_f$=0.15 in 10% triethylamine in methanol) in 1:1 methylene chloride/ethyl ether afforded compound 1b (39%) as pale yellow solid: mp, 208°-210° C.; IR (KBr) 3,300, 3,120-2,730, 1,650, 1,620, 1,580, 1,490, 1,435, 1,410, 1,250 cm$^{-1}$; $^1$H NMR (CDCl$_3$) δ 8.66 (br s, 1H), 7.50 (d, J=9.0 Hz, 1H), 7.25 (br m, 1H), 7.20 (s, 1H), 6.58 (d, J=9.0 Hz, 1H), 3.98 (s, 3H), 3.63-3.60 (m, 2H), 3.14 (t, J=5.7 Hz, 2H), 2.47-2.43 (m, 2H), 1.78 (br s, 1H); $^{13}$C NMR (proton coupled, CDCl$_3$) δ 160.0 (s), 140.1 (s), 128.5 (s), 125.4 (s), 122.7 (d), 122.0 (d) 121.8 (d), 117.0 (s), 105.5 (d), 53.2 (q), 45.5 (t), 43.4 (t), 27.4 (t); LRMS (m/z relative intensity) 230 (27), 229 (M+, 100), 228 (38), 214 (49), 212 (22), 199 (22), 197 (42), 187 (26), 186 (33), 185 (32), 171 (41); HRMS calculated for C$_{13}$H$_{15}$N$_3$O:229.1215, found: 229.1185.

D.
5-Ethoxy-3-(1,2,5,6-tetrahydropyridyl)pyrrolo[3,2-b]pyridine (1c)

The reaction time was 5 hours. Flash chromatography using silica gel and elution with 10% triethylamine in methanol yielded Compound 1c (48%) as a yellow powder mp, 186°-189° C.; IR (KBr) 3,430-2,810, 1,645, 1,610, 1,575, 1,480, 1,475, 1,435, 1,410, 1,275, 1,230 cm$^{-1}$; $^1$H NMR (DMSO-d$_6$) δ 11.2(br s, 1H), 7.68 (d, J=8.8 Hz, 1H), 7.45 (s,1H), 7.06 (br m, 1H), 6.54 (d, J=8.7 Hz, 1H), 4.4 (br s, 1H), 4.33 (q, J=7.0 Hz, 1H), 3.47 (br m, 2H), 2.99 (br m, 2H), 2.41 (br m, 2H) 1.35 (t, J=7.0 Hz, 6H); $^{13}$C NMR (DMSO-d$_6$) δ 158.3, 139.4, 128.6, 125.4, 124.2, 122.5, 119.5, 115.1, 104.6, 60.5, 44.4, 42.4, 26.8, 14.7; LRMS (m/z, relative intensity) 244 (M+, 100), 214 (81), 197 (94), 185 (33), 171 (49); HRMS calculated for C$_{14}$H$_{17}$N$_3$O:243.1372, found: 243.1367.

E.
5-Propoxy-3-(1,2,5,6-tetrahvdropyridy)pyrrolo[3,2-b]pyridine (1d)

The reaction time was 6 hours. Flash chromatography using silica gel and elution with 10% triethylamine in methanol yielded Compound 1d (78%) as a yellow foam; mp, 170°-173° C.; IR (KBr) 1,640, 1,620, 1,575, 1,470, 1,455, 1,410, 1,270, 1,235 cm$^{-1}$; $^1$H NMR (DMSO-d$_6$) δ 11.1 (br s, 1H), 7.67 (d, J=8.8 Hz, 1H), 7.42 (s, 1H), 7.06 (br s 1H), 6.55 (d, J=8.7 Hz, 1H), 4.24 (q, J=6.6 Hz, 1H), 3.41 (br m, 2H), 2.93 (t, J=5.6 HZ, 2H), 2.36 (br m, 2H), 1.82-1.71 (m, 2H), 0.98 (t, J=7.4 Hz, 6H); $^{13}$C NMR (DMSO-d$_6$) δ 158.5, 139.5, 128.5, 125.4, 123.9, 122.4, 120.8, 115.4, 104.6, 66.4, 45.0, 42.9, 27.3, 22.0, 10.7; LRMS (m/z, relative intensity), 258 (20), 257 (M+, 95), 215 (20), 214 (91), 198 (26), 197 (100), 185 (38), 172 (20), 171 (53), 169 (28); HRMS calculated for C.  257.1528, found: 257.1536.

F.
5-Isopropoxy-3-(1,2,5,6-tetrahydropvridyl)pyrrolo[3,2-b]pyridine (Compound 1e)

The reaction time was 6 hours. Flash chromatography of the extraction residue using silica gel (approximately 100 g) and elution with 5% triethylamine in methanol yielded Compound 1e (60%) as a pale yellow foam; IR (KBr) 3,400-2,800 (br), 1,650, 1,615, 1,580 1,470, 1,415, 1,385, 1,370 cm$^{-1}$; $^1$H NMR (DMSO-d$_6$) δ 7.64 (d, J=8.5 Hz, 1H) (br m, 1H), 7.03 (br m, 1H), 6.47 (d, J=8.6 Hz, 1H), 5.25 (sept, J=6.3 Hz, 1H), 3.40 (br m, 2H), 3.04 (br s, 1H), 2.93 (t, J=5.2 Hz, 2H), 2.36 (br m, 2H), 1.31 (d, J=6.3 Hz, 6H); $^{13}$C NMR (DMSO-d$_6$) δ 157 8, 139.5, 128.6, 125.2, 124.0, 122.4, 120.4, 115.3, 105.1, 66.7, 44.9, 42.8, 27.2, 22.0; LRMS (m/z, relative intensity) 258 (10), 257 (M+, 69), 214 (79), 197 (100), 185 (22), 172 (22); HRMS calculated for C$_{15}$H$_{19}$N$_3$O 257.1528, found: 257.1535.

G.
5-Butoxy-3-(1,2,5,6-tetrahydropyridyl)pyrrolo[3,2-b]pyridine (1f)

The reaction time was 19 hours. Flash chromatography using silica gel and elution with 5% triethylamine in methanol yielded a yellow solid. Cold methanol was added to this solid to prepare a slurry. The undissolved solid was filtered to yield Compound 1f (29%) as a yellow powder: mp, 158°-160° C.; IR (KBr) 2,950-2,620, 1,640, 1,620, 1,575, 1,500, 1,470, 1,450, 1,440, 1,410, 1,380 cm$^{-1}$; $^1$H NMR (DMSO-d$_6$) δ 11.1 (br s, 1H), 7.66 (d, J=8.7 Hz, 1H), 7.42 (s, 1H), 7.07 (br m, 1H), 6.53 (d, J=8.7 Hz, 1H), 4.29 (t, J=6.6 Hz, 1H), 3.41 (br m, 2H), 2.93 (br t, 2H), 2.36 (br m, 2H), 1.78-1.68 (m, 2H), 1.50-1.38 (m, 2H), 0.94 (t, J=7.4 Hz, 6H); $^{13}$C NMR (DMSO-d$_6$) δ 158.4 139 5, 128.5, 125.4, 123.9, 122.4, 120.8, 115.4, 104.6, 64.5, 45.0, 42.9, 30.7, 27.2, 19.0, 13.8; LRMS (m/z, relative intensity) 272 (54), 271 (98, M+), 270 (23), 243 (13), 228 (11), 215 (28), 214 (100), 212 (30), 198 (35), 197 (97), 187 (21), 185 (43), 172 (28), 171 (62), 169 (34); Anal. calculated for C$_{16}$H$_{21}$N$_3$O: C, 70.82; H, 7.80; N, 15.48; found: C, 70.17 H, 7.86; N, 15.26.

H.
5-t-Butoxy-3-(1,2,5,6-tetrahydropyridyl)pyrrolo[3,2-b]pyridine (1g)

The reaction time was 18 hours. Flash chromatography using silica gel and elution with 5% triethylamine in methanol yielded Compound 1g (48%) as a yellow foam: IR (KBr) 1,650, 1,610, 1,575, 1,480, 1,450, 1,410, 1,180 cm$^{-1}$; $^1$H NMR (DMSO)d$_6$ δ 11.5 (br s, 1H), 7.67 (d, J=8.8 Hz, 1H), 7.58 (s, 1H), 6.99 (br s, 1H), 6.48 (d, J=8.7 Hz, 1H), 3.73 (br m, 2H), 3.28 (br t, 2H) 2.74 (br m, 2H) 1.58 (s, 9H); LRMS (m/z, relative intensity) 271 (M+, 16), 215 (71), 214 (86), 198 (43), 197 (75), 186 (25), 185 (38), 173 (32), 172 (100), 171 (25), 169 (20); HRMS calculated for C$_{16}$H$_{21}$ N$_3$O: 271.1685, found: 271.1681.

I. 5-Benzyloxy-3-(1,2,5,6-tetrahydropyridyl)pyrrolo[3,2-b]pyridine (1h)

The reaction time was 6 hours. Flash chromatography using silica gel and elution with 5% triethylamine in methanol yielded Compound 1 h (40%) as a yellow solid which was converted to its maleic acid salt: mp, 185°-187° C.; IR (KBr) 1,645, 1,610, 1,580, 1,480, 1,465, 1,415, 1,365, 1,275 cm$^{-1}$: $^1$H NMR (DMSO-d$_6$) δ 11.4 (br s, 1H), 8.9 (br s, 2H), 7.76 (d, J=8.8 Hz, 1H), 7.62 (d, J=2.9 Hz, 1H), 7.49-7.47 (m, 2H), 7.40-7.28 (m, 3H), 7.05 (br s, 1H), 6.68 (d, J=8.7 Hz, 1H), 6.05 (s, 2H), 5.39 (s, 2H), 3.81 (br m, 2H), 3.36 (t, J=6.0 Hz, 2H), 2.71 (br m, 2H); $^{13}$C NMR (DMSO-d$_6$) δ 167.3, 158.3, 139.1, 138.2, 136.1, 128.5, 128.3, 127.8, 127.5, 125.6, 125.4, 123.0, 113.2, 112.9, 105.2, 66.7, 41.7, 40.4, 23.1; LRMS (m/z, relative intensity) 305 (M+, 4), 264 (3), 228 (8), 214 (96), 197 (100), 91 (75), 72 (28); HRMS calculated for C$_{19}$H$_{19}$N$_3$O: 305.1528, found: 305.1542.

J.
5-Cyclopentoxy-3-(1,2,5,6-tetrahydropyridyl)pyrrolo[3,2-b]pyridine (1i)

The reaction time was 24 hours. Flash chromatography using silica gel and elution with 5% triethylamine in methanol yielded Compound 1i (78%) as a yellow solid which was converted to its maleic acid salt: mp, 210°-211° C.; $^1$H NMR (DMSO-d$_6$) δ 11.3 (br s, 1H), 8.8 (br s, 2H), 7.70 (d, J=8.8 Hz, 1H), 7.60 (d, J=2.9 Hz, 1H), 7.10 (br m, 1H), 6.54 (d, J=8.8 Hz, 1H), 6.05 (s, 2H), 5.40-5.35 (m, 1H), 3.82 (br m, 2H), 3.37 (t, J=6.0 Hz, 2H), 2.73 (br m, 2H), 2.02-1.93 (m, 2H), 1.80-1.57 (m, 6H); $^{13}$C NMR (DMSO-d$_6$) δ 167.3, 158.4, 139.4, 136.1, 128.8, 125.3, 125.2, 122.8, 113.2, 112.6, 105.6, 76.8, 41.7, 32.6, 23.8, 23.1; LRMS (m/z, relative intensity) 283 (26), 215 (24), 214 (100), 198 (38), 197 (83), 185 (28), 173 (23), 172 (71), 171 (26), 169 (23), 121 (30), 72 (50); HRMS calculated for C$_{17}$H$_{21}$N$_3$O: 283.1684, found: 283.1684.

K.
5-Hydroxy-3-(1,2,5,6-tetrahydropyridyl)pyrrolo[3,2-b]pyridine (Compound 1j)

The reaction time was 6 hours. Flash chromatography of the extraction residue using silica gel (approximately 100 g) and elution with 10% triethylamine in methanol yielded a white foam. This foam was triturated in 5% methanol/ethyl acetate to yield Compound 1j (65%) as an off-white solid: mp, decomposes 248.0° C.; IR (KBr) 3,280 1,620, 1,450, 1,415, 1,385, 1,340 cm$^{-1}$; $^1$H NMR (DMSO-d$_6$) δ 11.1 (br s, 1H), 7.56 (d, J=9.3 Hz, 1H), 7.23 (s, 1H), 6.39 (br m, 1H), 6.15 (d, J=8.9 Hz, 1H), 3.33 (br m, 2H), 2.88 (t, J=5.6 Hz, 2H), 2.26 (br m, 2H); $^{13}$C NMR (DMSO-d$_6$) δ 161.0, 132.3, 127.7, 126.2, 122.6, 121.8, 121.2, 112.9, 109.4, 44.7, 42.8, 27.8; LRMS (m/z, relative intensity) 216 (27), 215 (M+, 100), 214 (25), 198 (30), 197 (52), 186 (36), 185 (49), 173 (29), 172 (75), 171 (34), 147 (21); HRMS calculated for C$_{12}$H$_{13}$N$_3$O: 215.1058, found: 215.1032.

L.
5-Chloro-3-(1,2,5,6-tetrahydropyridyl)pyrrolo[3,2-b]pyridine (Compound 1k)

The reaction time was 6 hours. Flash chromatography of the extraction residue using silica gel (approximately 100 g) and elution with 10% triethylamine in methanol, followed by crystallization of the recovered oil using ethyl acetate yielded Compound 1k (38%) as a pale yellow solid: mp, 178-180° C.; IR (KBr) 3,400, 3,120-2,600, 1,650, 1,620, 1,555, 1,490, 1,410, 1,425 cm$^{-1}$; $^1$H NMR (DMSO-d$_6$) δ 11.54 (br s, 1H), 7.81 (d, J=8.6 Hz, 1H), 7.66 (s, 1H), 7.14 (d, J=8.0 Hz, 1H), 6.95 (br m, 1H), 3.39 (br m, 2H), 3.25 (br s, 1H), 2.92 (t, J=5.6 Hz, 2H), 2.36 (br m, 2H); LRMS (m/z relative intensity) 235 (21), 234 (17), 233 (M+, 74), 232 (33), 218 (25), 217 (20), 215 (27), 205 (32), 204 (36), 203 (41), 192 (43), 191 (47), 190 (100), 167 (21), 165 (36), 98 (28); HRMS calculated for C$_{12}$H$_{12}$N$_3$Cl: 233.0720, found: 233.0681.

M.
5-Dimethylamino-3-(1,2,5,6-tetrahydropyridyl)pyrrolo[3,2-b]pyridine (Compound 1l)

The reaction time was 6 hours. Trituration of the extraction residue using ethyl acetate yielded Compound 1l (17%) as a pale yellow powder: mp, decomposes at 120° C.; IR (KBr) 1,610, 1,580, 1,490, 1,405, 1,365 cm$^{-1}$; $^1$H NMR (DMSO-d$_6$) δ 7.53 (d, J=8.9 Hz, 1H), 7.31 (s, 1H), 7.13 (br m, 1H), 6.54 (d, J=8.9 Hz, 1H), 4.02 (br m, 2H), 3.44 (br m, 2H), 3.01 (s, 6H), 2.38 (br m, 2H); LRMS (m/z relative intensity) 243 (20), 242 (M+, 100), 227 (32), 214 (20), 210 (24), 209 (23), 196 (22), 184 (24); HRMS calculated for C$_{14}$H$_{18}$N$_4$: 242.1532, found: 242.1536.

N.
5-Methyl-3-(1,2,5,6-tetrahydropyridyl)pyrrolo[3,2-b]pyridine (Compound 1m)

The reaction time was 23 hours. Flash chromatography using silica gel and elution with 5% triethylamine in methanol yielded Compound 1m (49%) as a yellow glass which was converted to its maleic acid salt: mp, 158°-159° C. with decomposition; IR (KBr) 1,640, 1,610, 1,570 1,510, 1,415, 1,385, 1,370 cm$^{-1}$; $^1$H NMR (DMSO-d$_6$) δ 11.3 (br s, 1H), 8.8 (br s, 2H), 7.69-7.67 (m, 2H), 7.23 (br m, 1H), 7.03 (d, J=8.3 Hz, 1H), 6.04 (s, 2H), 3.82 (br m, 2H), 3.36 (br m, 2H), 2.73 (br m, 2H), 2.56 (s, 3H); LRMS (m/z, relative intensity) 214 (12), 213 (M+, 100), 212 (39), 198 (26), 185 (28), 184 (32), 183 (36), 171 (32), 170 (56), 72 (34); HRMS calculated for C$_{13}$H$_{15}$N$_3$: 213.1258, found: 213.1268.

O. 3-(1,2,5,6-Tetrahydropyridyl)pyrrolo[3,2-c]pyridine (Compound 2)

The reaction time was 2 hours. Flash chromatography of the extraction residue using silica gel (approximately 200 g) and elution with 5% triethylamine in methanol yielded Compound 2 (8%) as a pale yellow solid: mp, 200°-202° C.; IR (KBr) 3,400, 3,240-2,740, 1,640, 1,575, 1,535, 1,470, 1,445, 1,350 cm$^1$; $^1$H NMR (DMSO-d$_6$) δ 11.7 (br s, 1H), 9.17 (s, 1H), 8.22 (d, J=8.5 Hz, 1H), 7.45 (s, 1H), 7.36 (d, J=8.5 Hz, 1H). 6.29 (br s, 1H), 3.42 (br m, 2H), 2.95 (br m, 2H), 2.40 (br m, 2H); $^{13}$C NMR (DMSO-6) δ 142.8, 140,3, 140.1, 129.2, 123.1, 121.9, 121.3, 116.7, 106.9, 44.7, 42.6, 27.9; LRMS (m/z, relative intensity) 200 (34), 199 (M+, 100), 198 (84), 171 (29), 170 (74), 169 (36), 155 (20), 143 (13), 131 (42), 119 (19); HRMS calculated for C$_{12}$H$_{13}$N$_3$: 199.1110, found: 199.1071.

P. 3-(1,2,5,6-Tetrahydropyridyl)pyrrolo[2,3-c]pyridine (Compound 3a)

The reaction time was 4 hours. Flash chromatography of the extraction residue using silica gel (approximately 200 g) and elution with 5% triethylamine in methanol yielded compound 3a (28%) as a pale yellow solid: mp, 208°-210° C.; IR (KBr) 3,220, 3,120-2,740, 1,640, 1,500, 1,460, 1,430, 1,260, 1,140 cm$^{-1}$; $^1$H NMR (DMSO-d$_6$) 8.71 (d, J=1.7 Hz, 1H), 8.09 (d, J=5.6 Hz, 1H), 7.74 (dd, J=1.6 and 5.6 Hz, 1H), 7.59 (s, 1H), 6.19 (br m, 1H), 3.39 (d, J=3.0 Hz, 2H), 3.28 (br s, 1H), 2.92 (t, J=5.8 Hz, 2H), 2.38 (br m, 2H); $^{13}$C NMR (DMSO-d$_6$) δ 138.1, 134.8, 134.0, 129.3, 128.6, 126.0, 120.6, 116.2, 114.6, 44.7, 42.7, 27.9; LRMS (m/z, relative intensity) 200 (14), 199 (M+100), 198 (76), 170 (49), 169 (25), 156

Q.
5-Methoxy-3-(1,2,5,6-tetrahydropyridyl)pyrrolo[2,3-c]pyridine (Compound 3b)

The reaction time was 4 hours. Trituration of the extraction residue with methylene chloride afforded a pale yellow solid. This solid was dissolved with methanol/methylene chloride, and maleic acid (1.05 eq) was added to this solution. Addition of ethyl ether triturated the maleate salt of Compound 3b (40%) as a pale yellow powder: mp, decomposes 170° C.; IR (KBr) 3,100–2,600, 1,720, 1,630, 1,480, 1,370, 1,230 cm$^{-1}$; $^1$H NMR (DMSO-d$_6$) δ 11.57 (br s, 1H), 8.87 (br s, 2H), 8.40 (s, 1H), 7.75 (s, 1H), 7.14 (s, 1H) 6.14 (br m, 1H), 6.09 (s, 2H), 3.85 (s, 3H), 3.78 (br m, 2H), 3.36 (br t, 2H), 2.71 (br m, 2H); $^{13}$C NMR (DMSO-d$_6$) δ 167.3, 157.9, 135.4, 132.9, 131.5, 130.6, 129.8, 129.3, 113.3, 112.4, 97.3, 53.6, 41.6, 23.9; LRMS (m/z, relative intensity) 230 (19), 229 (M+, 100), 228 (77), 212 (24), 201 (63), 200 (65), 199 (27), 185 (46), 150 (20), 114 (33), 99 (54), 87 (21), 57 (78); HRMS calculated for C$_{13}$H$_{15}$N$_3$O: 229.1215, found: 229.1232.

R.
5-Chloro-3-(1,2,5,6-tetrahydropyridyl)pyrrolo[2,3-c]pyridine (Compound 3c)

The reaction time was 9 hours. Trituration of the extraction residue with ethyl acetate afforded Compound 3c (54%) as a pale yellow powder: mp, 230°–233° C.; IR (KBr) 3,420, 3,240, 1,610, 1,545, 1,450 cm$^{-1}$: $^1$H NMR (DMSO-d$_6$) δ 8.52 (s, 1H), 7.77 (s, 1H), 7.71 (s, 1H), 6.16 (br m, 1H), 3.38 (br m, 2H), 3.20 (br s, 1H), 2.91 (t, J=5.3 Hz, 2H), 2.35 (br m, 2H); $^{13}$C NMR (DMSO-d$_6$) δ 139.4, 134.0, 133.4, 131.8, 128.7, 128.6, 121.8, 116.3, 113.7, 44.8, 42.7, 28.1; LMRS (m/z, relative intensity) 235 (48), 234 (53), 233 (M+, 100), 232 (94), 206 (21), 204 (53), 169 (27), 165 (24); HRMS calculated for C$_{12}$H$_{12}$N$_3$Cl: 233.0720, found: 233.0671.

S. 3-(1,2,5,6-Tetrahydropyridyl)pyrrolo[2,3-b]pyridine (Compound 4)

The reaction time was 4 hours. Trituration of the extraction residue with ethyl acetate afforded Compound 4 (63%) as a pale yellow solid: mp, 199.0°–202.0° C.; IR (KBr) 3,280, 3,100–2,740, 1,650, 1,595, 1,570, 1,520, 1,495, 1,450, 1,415, 1,330, 1,240 cm$^{-1}$; $^1$H NMR (DMSO-d$_6$) δ 11.65 (br s, 1H), 8.20 (d, J=6.7 Hz, 1H), 7.47 (s, 1H), 7.08–7.03 (m, 2H), 6.18 (br m, 1H), 3.39–3.34 (br m, 2H), 2.92 (br m, 2H), 2.37 (br m, 2H); LRMS (m/z, relative intensity) 200 (21), 199 (M+, 100), 198 (77), 171 (22), 170 (87), 169 (36), 155 (22), 143 (22), 142 (23), 131 (67), 80 (23); HRMS calculated for C$_{12}$H$_{13}$N$_3$: 199.1110, found: 199.1059.

EXAMPLE 2
(6-Chloro-3-nitro-2-pyridyl)acetonitrile (Compound 5a) and (6-chloro-3-nitro-4-pyridyl)acetonitrile (Compound 6)

To a stirred solution of potassium tert-butoxide (24.69 g, 220 mmol, 2.2 eq) in anhydrous tetrahydrofuran (150 ml) at −50° C. under nitrogen, a solution of 2-chloro-5-nitropyridine (15.85 g, 100 mmol) and (4-chlorophenoxy)acetonitrile (E. Grochowski et al., *Bull. Acad. Pol. Sci. Ser. Sci. Chim.* 11, 443 (1963)) (18.44 g, 110 mmol, 1.1 eq)- in anhydrous tetrahydrofuran (150 ml) was added dropwise at such a rate that the reaction temperature was maintained at −40° to −50° C. with cooling in a dry ice/acetone bath. The resultant purple colored reaction mixture was then stirred at −78° C. under nitrogen for 1 hour, at which time glacial acetic acid (20 ml, 0.35 mol, 3.5 eq) was added to the reaction, and the mixture was allowed to warm to room temperature. A solution of 5% HCl (100 ml) was added to the reaction mixture and this aqueous mixture was extracted with ethyl ether (100 ml) and then with methylene chloride (2×100 ml). The extracts were combined, dried (MgSO$_4$), and passed through a silica gel filter (approximately 150 g) followed by methylene chloride (1,200 ml). This filtrate was evaporated under reduced pressure, and the residual oil was chromatographed using silica gel (approximately 300 g) and eluted with 25% hexanes in methylene chloride to afford an oil (R$_f$=0.52 in methylene chloride) which was triturated in cold anhydrous ether to afford Compound 5a (1.37 g, 7%) as a white crystalline solid: mp, 121.5°–123.5° C.; IR (KBr) 3,070, 2,240, 1,600, 1,560, 1,525, 1,430, 1,390 1,370, 1,345, 1,185 cm$^{-1}$; $^1$H NMR (CDCl$_3$) δ 8.45 (d, J=8.6 Hz, 1H), 7.56 (d, J=8.6 Hz, 1H), 4.38 (s, 2H); $^{13}$C NMR (CDCl$_3$)δ 155.5, 146.8, 143.2, 136.2, 125.5, 114.4, 26.7; LRMS (m/z, relative intensity) 199 (10), 198 (12), 197 (M+, 30), 170 (23), 151 (39), 126 (75), 125 (20), 124 (100), 116 (29), 115 (54), 112 (23), 99 (49), 88 (24), 79 (75); Anal. calc'd for C$_7$H$_4$Cl$n_3$O$_2$: C, 42.55; H, 2.04; N, 21.27; found: C, 42.52; H, 1.89; N, 20.95.

Further elution yielded another oil (R$_f$=0.48 in methylene chloride) which was triturated in cold anhydrous ethyl ether to afford Compound 6 (1.87 g, 9%) as a white crystalline solid: mp, 87°–89° C.; IR (KBr) 3,080, 2,240, 1,600, 1,545, 1,520, 1,450, 1,390, 1,340, 1,135 cm$^{-1}$; $^1$H NMR (CDCl$_3$) δ 9.17 (s, 1H), 7.76 (s, 1H), 4.27 (s, 2H); $^{13}$C NMR (CDCl$_3$) δ 157.4, 147.3, 137.7, 125.5, 114.4, 22.5; LRMS (m/z, relative intensity) 199 (39), 197 (M+, 100), 182 (28), 180 (70), 153 (29), 152 (31), 151 (67), 127 (29), 126 (61), 125 (35), 124 (64), 116 (32), 115 (47), 114 (35), 99 (33), 98 (21), 97 (46); Anal. calc'd for : C, 42.55; H, 2.04; N, 21.27, found: C, 42.35; H, 1.95; N, 20.94.

EXAMPLE 3
(6-Chloro-3-nitro-2-pyridyl)acetonitrile (Compound 5a)

To a stirred solution of NaH (60%, 1.84 g, 46 mmol, 2.3 eq) and ethyl cyanoacetate (4.90 ml, 46 mmol, 2.3 eq) in anhydrous tetrahydrofuran (30 ml) at 0° C., a solution of 2,6-dichloro-3-nitropyridine (3.86 g, 20.0 mmol) in anhydrous tetrahydrofuran (20 ml) was added dropwise. The resulting reaction mixture was stirred at 0° C. under nitrogen for 90 minutes, during which time the reaction slowly changed color from yellow to deep red. A solution of 5% HCl (40 ml) was then added to the reaction mixture, and this aqueous mixture was extracted with ether (40 ml) and then methylene chloride (40 ml). The extracts were combined, dried (MgSO$_4$), and evaporated under reduced pressure. The residual oil was passed through a silica gel filter (approximately 200 g) followed by 10% ethyl acetate/hexanes (1.5 L), 2:1 hexanes/ethyl acetate (2 L), and 1:1 ethyl acetate/hexanes (1 L). The latter 3 L were evaporated under reduced pressure to yield a clear, pale yellow oil (7.2 g). This oil was placed in an aqueous solution of 2M HI (30 ml), and this mixture was heated at reflux for 5 hours. The resultant reaction mixture was extracted with methylene chloride (3×30 ml), and these extracts were combined, dried (MgSO$_4$), and passed through a silica gel filter (approximately 150 g) followed by methylene chloride (1 L). This filtrate was evaporated under reduced pressure, and the residual solid was stirred in cold ahydrous ethyl ether. The undissolved solid was filtered to afford Compound 5a (1.16 g, 5.87 mmol, 29% overall) as an off-white, crystalline solid: mp, 119°–121° C. The physical and spectral properties of this solid were identical to the physical and spectral properties of the Compound 5a described in Example 2.

EXAMPLE 4

6-Benzyloxy-3-nitro-2-pyridyl)acetonitrile (Compound 5b)

To a stirred solution of potassium tert-butoxide (12.34 g, 110 mmol, 2.2 eq) in anhydrous dimethylformamide (100 mL) at −10° C. was added dropwise a solution of (4-chlorophenoxy)acetonitrile (9.22 g, 55 mmol, 1.1 eq) and 2-benzyloxy-5-nitropyridine (H. L. Friedman et al., J. Am. Chem. Soc., 69, 1204 (1947)) (11.51 g, 50.0 mmol) in anhydrous dimethylformamide (50 mL). The resultant deep purple-colored solution was stirred at −10° C. under nitrogen for 1 hour. Then an aqueous 5% HCl solution 85 mL) added dropwise to the reaction solution at 0° C., and the precipitated solid was filtered and dried to yield a brown solid (13.4 g). This solid was dissolved in methylene chloride (50 mL), and this solution was passed through a silica gel filter (approximately 500 g) followed by an elution of methylene chloride (4 L). This filtrate was evaporated under reduced pressure, and the residual oil crystallized in ethyl ether/hexanes (1:1) to yield Compound 5b (11.15 g, 41.4 mmol, 83%) as an off-white solid: mp, 63.0°–67.0° C.; IR (KBr) 2,260, 1,590, 1,515, 1,470, 1,455 1,450, 1,420, 1,350, 1,295 cm$^{-1}$; $^1$H NMR (CDCl$_3$) δ 8.41 (d, J=8.8 Hz, 1H), 7.56–7.31 (m, 5H), 6.90 (d, J=8.8 Hz, 1H), 5.60 (s, 2H), 4.43 (s, 2H); LRMS (m/z, relative intensity) 270 (12), 269 (M+, 55), 107 (29), 92 (39), 91 (100), 65 (55). Anal. calcd. for C$_{14}$H$_{11}$N$_3$O$_3$: C, 62.45; H, 4.12; N, 15.61; found: C, 62.19; H, 4.05; N, 15.55.

EXAMPLE 5

6-Dimethylamino-3-nitro-2-pyridyl)acetonitrile (Compound 5c)

To a stirred solution of potassium tert-butoxide (12.34 g, 110 mmol, 2.2 eq) in anhydrous dimethylformamide (100 mL) at −10° C. was added dropwise a solution of (4-chlorophenoxy)acetonitrile (9.22 g, 55 mmol, 1.1 eq) and 2-dimethylamino-5-nitropyridine (Pfaltz and Bauer, Inc., 8.36 g, 50.0 mmol) in anhydrous dimethylformamide (50 mL). The resultant deep purple-colored solution was stirred at −10° C. under nitrogen for 1 hour. Then an aqueous 5% HCL solution (85 mL) added dropwise to the reaction solution at 0° C., and the precipitated solid was filtered and dried to yield Compound 5c (8.60 g, 41.7 mmol, 83%) as a yellow solid: mp, 156.0°–158.0° C.; IR (KBr) 2,240, 1,600, 1,580, 1,530, 1,485, 1,420, 1,385, 1,335 cm$^{-1}$; $^1$H NMR (CDCl$_3$) δ 8.25 (d, J=9.0 Hz, 1H), 6.45 (d, J=9.6 Hz, 1H), 4.38 (s, 2H), 3.25 (br s, 6H); LRMS (m/z, relative intensity) 207 ($^{13}$), 206 (M+, 100), 191 (54), 189 (26), 177 (88), 160 (35), 159 (22), 145 (94), 134 (30), 131 (24), 119 (29), 118 (59), 93 (27). Anal. calcd. for C$_9$H$_{10}$N$_4$O$_2$: C, 52,42; H, 4.89; N, 27.17; found: C, 52.19; H, 4.93; N, 26.93.

EXAMPLE 6

5-Chloropyrrolo[3,2-b]pyridine (Compound 7a)

A mixture of 500 mg Raney nickel (washed thoroughly with absolute ethanol), Compound 5 (1.70 g, 8.60 mmol), and 1:1 absolute ethanol/acetic acid (30 ml) was shaken under a hydrogen atmosphere (3 atm) for 2 hours. The reaction mixture was filtered, and the filtrate was evaporated under reduced pressure. The residual oil was placed in a saturated solution of sodium bicarbonate (10 ml), and this aqueous mixture was extracted with methylene chloride (3×25 ml). These extracts were combined, dried (MgSO$_4$), and evaporated under reduced pressure. The residual solid was stirred in cold anhydrous ethyl ether, and the undissolved solid was filtered to yield Compound 7a (0.65 g, 4.26 mmol, 50%) as a white solid: mp, 200°–203° C.; IR (KBr) 3,140–2,700, 1,620, 1,555, 1,500, 1,460, 1,450, 1,415, 1,335 cm$^{-1}$; $^1$H NMR (CDCl$_3$) δ 8.92 (br, s 1H), 7.67 (d, J=8.0 Hz, 1H), 7.48 (t, J=2.9 Hz, 1H), 7.11 (d, J=7.9 Hz, 1H), 6.67–6.65 (m, 1H); LRMS m/z, relative intensity) 154 (46), 153 (17), 152 (M+, 100), 117 (81), 90 (17), 63 (15); HRMS calculated for C$_7$H$_5$ClN$_2$: 152.0141, found: 152.0131 (1.0 ppm deviation).

EXAMPLE 7

A. 5-Alkoxypyrrolo[3,2-b]pyridines (Compound 7x)

To a stirred solution of potassium t-butoxide (12.34 g, 110 mmol, 2.2 eq) in anhydrous dimethylformamide or tetrahydrofuran (referred to below as the reaction medium) cooled at −10° C. under a nitrogen atmosphere was added dropwise a solution of (4-chlorophenoxy)acetonitrile (9.22 g, 55 mmol, 1.1 eq) and 2-alkoxy-5-nitropyridine (50 mmol) in anhydrous dimethylformamide or tetrahydrofuran (All 2-alkoxy-5-nitropyridines were prepared using the methodology of H. L. Friedman, et al., J. Am. Chem. Soc., 69, 1,204 (1947), with minor modifications in reaction times, temperatures and methods of purification). The resulting deep purple reaction solution was then maintained at −10° C. under nitrogen for 1 hour. Aqueous hydrochloric acid was added (80 mL, 5% HCl), and the resulting mixture was allowed to warm to room temperature. The reaction mixture was extracted with methylene chloride (3×50 mL), and these extracts were combined, dried (MgSO$_4$), and evaporated under reduced pressure. The residual oil was passed through a silica gel filter (approximately 200 g) followed by methylene chloride/hexanes (1:1, 2L). This filtrate was evaporated under reduced pressure, and the residual oil (containing the desired (6-alkoxy-3-nitro-2-pyridyl)acetonitrile) was dissolved in acetic acetic and 10% palladium/carbon was added (10% by weight of oil). This mixture was hydrogenated under 3 atm hydrogen for 6 hours. The resulting mixture was filtered through diatomaceous earth (Celite (trademark)), and the filtrate was evaporated under reduced pressure. The residual oil was placed in water (50mL), and the pH was adjusted to 10 with addition of sodium carbonate. This mixture was extracted with methylene chloride (2×100 mL), and these extracts were combined, dried (MgSO$_4$), and evaporated under reduced pressure. Chromatography using silica gel (approximately 200 g) and elution with the appropriate solvent system yielded the desired 5-alkoxypyrrolo[3,2-b]pyridine (Compound 7x). The compounds prepared are described more specifically below.

B. 5-Ethoxypyrrolo[3,2-b]pyridine (Compound 7b)

The reaction solvent was tetrahydrofuran. Elution first with methylene chloride and then with methylene chloride/ethyl ether (9:1) yielded Compound 7b (19%) as a yellow solid: mp, 156°-157.5° C.; IR (KBr) 1,620, 1,570, 1,485, 1,470, 1,445, 1,410, 1,390, 1,365, 1,340, 1,305 cm$^{-1}$; $^1$H NMR (CDCl$_3$) δ 8.35 (br s, 1H), 7.55 (d, J=8.5 Hz, 1H), 7.28 (t, J=3.2 Hz, 1H), 6.58 (d, J=9.0 Hz, 1H), 6.57-6.55 (m, 1H), 4.41 (q, J=7.0 Hz, 2H), 1.40 (t, J =7.1 Hz, 3H); LRMS (m/z, relative intensity) 163 (32), 162 (M+, 89), 147 (100), 134 (85), 119 (22), 118 (75), 117 (31), 106 (83), 105 (48), 79 (49); Anal. calcd. for C$_9$H$_{10}$N$_2$O: C, 66.65; H, 6.21; N, 17.27; found: C, 66.31; H, 6.18; N, 17.15.

C. 5-Propoxypyrrolo[3,2-b]pyridine (Compound 7c)

The reaction solvent was tetrahydrofuran. Elution first with methylene chloride and then with 1% methanol in methylene chloride yielded Compound 7c (23%) as a yellow solid: mp, 114°-116° C.; IR (KBr) 1,615, 1,610, 1,585, 1,475, 1,410, 1,380, 1,305 cm$^{-1}$; $^1$H NMR (CDCl$_3$) δ 8.1 (br s, 1H), 7.57 (d, J=8.7 Hz, 1H), 7.31-7.29 (m, 1H), 6.60 (d, J=8.9 Hz, 1H), 6.59-6.57 (m, 1H), 4.31 (t, J= 6.8 Hz, 2H), 1.88-1.76 (m, 2H), 1.04 (t, J=7.4 Hz, 3H); $^{13}$C NMR (CDCl$_3$) δ 158.8, 142.4, 127.6, 124.2, 122.3, 104.6, 100.9, 66.4, 22.1, 10.6; Anal. calcd. for C$_{10}$H$_{12}$N$_2$O: C, 68.16; H, 6.86; N, 15.90,; found: C, 67.56; H, 6.43; N, 15.71.

D. 5-Isopropoxypyrrolo[3,2-b]pyridine (Compound 7d)

The reaction solvent was tetrahydrofuran. Elution first with ether/hexanes (1:2, 4,000 mL) and then with ether/hexanes (1:1) yielded Compound 7d (16% from isolated (6-isopropoxy-3-nitro-2-pyridyl)acetonitrile) as an off-white solid: mp, 104.5°-107.5°; IR (KBr) 1,620, 1,575, 1,480, 1,455, 1,410, 1,390, 1,335, 1,310 cm$^{-1}$; $^1$H NMR (CDCl$_3$) δ 8.77 (br m, 1H), 7.54 (d, J=9.0 Hz, 1H), 7.28 (t, J=2.9 Hz, 1H), 6.54 (d, J=8.4 Hz, 1H), 6.52 (br m, 1H), 5.38 (sept, J=6.3 Hz, 1H), 1.35 (d, J=6.3 Hz, 6H); $^{13}$C NMR (CDCl$_3$) δ 159.4, 142.8, 126.6, 124.3, 122.0, 106.5, 102.4, 67.7, 22.2; LRMS (m/z, relative intensity) 177 (7), 176 (M+, 51), 161 (30), 134 (100), 106 (57), 79 (20). Anal. calc'd for C$_{10}$H$_{12}$N$_2$O: C, 68.16; H, 6.86; N, 15.90; found: C, 67.95; H, 6.77; N, 15.81.

E. 5-Butoxypyrrolo[3,2-b]pyridine (7e)

The reaction solvent was tetrahydrofuran. Elution with a 1-3% methanol gradient in methylene chloride yielded Compound 7e (36%) as an off-white solid: mp, 92°-93° C.; IR (KBr) 2,960-2,750, 1,620, 1,570, 1,490, 1,460, 1,415, 1,395, 1,340, 1,320 cm$^{-1}$; $^1$H NMR (CDCl$_3$) δ 8.5 (br s, 1H), 7.56 (d, J=8.9 Hz, 1H), 7.30 (t, J=3.0 Hz, 1H), 6.60 (d, J=8.8 Hz, 1H), 6.57 (m, 1H), 4.35 (t, J=6.7 Hz, 2H), 1.82-1.72 (m, 2H), 1.55-1.42 (m, 2H), 0.96 (t,J=7.4 Hz, 3H); $^{13}$C NMR (CDCl$_3$) δ 160.1, 142.5, 126.4, 124.1, 121.8, 106.0, 102.7, 65.7, 31.4, 19.4, 14.0; LRMS (relative intensity) 191 (26), 190 (67, M+), 160 (35), 147 (52), 135 (25), 134 (100), 118 (21), 117 (32), 106 (60), 105 (28), 78 (19); Anal. calc'd for C$_{11}$H$_{14}$N$_2$O: C, 69.45; H, 7.42; N, 14.72; found C, 69.20; H, 7.33; N, 14.58.

F. 5-t-Butoxypyrrolo[3,2-b]pyridine (Compound 7f)

The reaction solvent was tetrahydrofuran. Elution first with methylene chloride and then with 1% methanol in methylene chloride yielded a mixture, which was re-chromatographed using silica gel (approximately 100 g) and elution with ethyl ether/hexanes (1:1) to afford Compound 7f (15%) as an off-white solid: mp, 109°-110° C.; IR (KBr) 1,615, 1,570, 1,470, 1,450, 1,410, 1,390, 1,365, 1,300 cm$^{-1}$; $^1$H NMR (CDCl$_3$) δ 8.1 (br s, 1H), 7.52 (d, J=8.8 Hz, 1H), 7.29-7.27 (m, 1H), 6.56 (d, J=8.5 Hz, 1H), 6.55-6.53 (m, 1H), 1.57 (s, 9H); $^{13}$C NMR (CDCl$_3$) δ 159.1, 143.1, 126.6, 124.6, 121.1, 109.4, 103.0, 79.2, 29.0; LRMS (m/z, relative intensity) 190 (M+, 17), 135 (31), 134 (100), 106 (57), 105 (22), 79 (22),; Anal. calcd. for C$_{11}$H$_{14}$N$_2$O: C, 69.45; H, 7.42; N, 14.72; found: C, 69.37; H, 7.48; N, 14.49.

G. 5-Benzyloxypyrrolo[3,2-b]pyridine (Compound 7g)

The reaction solvent was dimethylformamide. Raney nickel (washed with ethanol) was used in place of palladium on carbon. Elution with methylene chloride yielded Compound 7g (27% from isolated (6-benzyloxy-3-nitro-2-pyridyl)acetonitrile) as an off-white solid: mp, 146.0°-148.0° C.; IR (KBr) 1,605, 1,580, 1,500, 1,470, 1,450, 1,410, 1,300 cm$^{-1}$; $^1$H NMR (CDCl$_3$) δ 8.47 (br m, 1H), 7.57 (d, J=9.0 Hz, 1H), 7.50-7.48 (m, 2H), 7.39-7.27 (m, 4 H), 6.67 (d, J=8.4 Hz, 1H), 6.60-6.58 (m, 1H), 5.45 (s, 2H); $^{13}$C NMR (CDCl$_3$) δ 159.7, 142.6, 137.8, 128.4, 128.0, 127.7, 126.7, 124.5, 122.1, 106.0, 102.6, 67.7; LRMS (M/z, relative intensity) 225 (38), 224 (M+, 89), 223 (40), 207 (20), 147 (61), 119 (31), 118 (75), 105 (30), 92 (22), 91 (100), 65 (36). Anal. calc'd for C$_{14}$H$_{12}$N$_2$O: C, 74.98; H, 5.39; N, 12.49; found: C, 74.80; H, 5.22; N, 12.42.

H. 5-Cyclopentoxypyrrolo[3,2-b]pyridine (Compound 7h)

The reaction solvent was tetrahydrofuran. Elution with 2.5% methanol in methylene chloride yielded a mixture which was triturated in ethyl ether, and the undissolved solid was filtered to yield Compound 7h (29%) as a white solid; mp, 99°-101° C.; IR (KBr) 1,610, 1,580, 1,480, 1,445, 1,510, 1,360, 1,320, 1,300 cm$^{-1}$; $^1$H NMR (CDCl$_3$) 8.1 (br s, 1H), 7.55 (d, J=8.8 Hz, 1H), 7.29 (t, J=2.9 Hz, 1H), 6.58-6.56 (m, 1H), 6.55 (d, J=8.7 Hz, 1H) 5.52-5.47 (m, 1H), 2.05-1.92 (m, 2H), 1.88-1.75 (m, 4H), 1.70-1.55 (m, 2H); LRMS (m/z, relative intensity) 203 (30, 202 (M+, 62), 174 (11), 159 (15), 135 (40), 134 (100), 133 (20), 117 (28), 106 (64), 105 (35), 79 (38); Anal. calc'd for C$_{14}$H$_{12}$N$_2$O[25 H$_2$O]: C, 69.71; H, 7.07; N, 13.54; found: C, 69.81; H, 6.66; N, 12.30.

EXAMPLE 8

5-Hydroxypyrrolo[3,4-b]pyridine (Compound 7i)

A mixture of 5-benzyloxypyrrolo[3,4-b]pyridine (Compound 7f, 1.38 g, 6.15 mmol), 5% Pd/C (0.30 g), and absolute ethanol (25 mL) was shaken under a hydrogen atmosphere (3 atm) for 30 minutes. The resulting mixture was filtered through diatomaceous earth (Celite (trademark)), and the filtrate was evaporated under reduced pressure. The residual solid was triturated in ethyl ether to yield Compound 7i (0.80 g, 5.96 mmol, 97%) as an off-white crystalline solid: mp, 280.0°-282.0° C.: IR (KBr) 1,640, 1,615, 1,605, 1,455, 1,430, 1,400, 1,380, 1,365 cm$^{-1}$; $^1$H NMR (DMSO-d$_6$) δ 11.4 (br m, 2H), 7.56 (d, J=9.7 Hz, 1H), 7.16 (d, J=3.1 Hz, 1H), 6.01-5.93 (m, 2H); $^{13}$C NMR (DMSO-d$_6$) 162.0, 131.9, 127.9, 125.0, 118.2, 112.2, 94.5; LRMS (m/z, relative intensity) 135 (41), 134 (M+, 100), 106 (66), 105 (42), 79 (59), 53 (31), 52 (52). Anal. calcd. for C$_7$H$_6$N$_2$O: C, 62.68; H, 4.51; N, 20.88; found: C, 62.40; H, 4.40; N, 20.76.

EXAMPLE 9

5-Dimethylaminopyrrolo[3,2-b]pyridine (Compound 7j)

A mixture of (6-dimethylamino-3-nitro-2-pyridyl)acetonitrile (Compound 5c, 2.06 g, 10.0 mmol), Raney nickel (0.70 g, washed thoroughly with absolute ethanol), and absolute ethanol/acetic acid (4:1, 50 mL) was shaken under a hydrogen atmosphere (3 atm) for 3 hours. The resulting mixture was filtered through diatomaceous earth (Celite (trademark)), and the filtrate was evaporated under reduced pressure. The residual oil was dissolved in water (25 mL), the pH was adjusted to 10 with sodium carbonate, and the mixture was extracted with methylene chloride (3×25 mL). These extracts were combined, dried (MgSO$_4$), and evaporated under reduced pressure to yield an oil. This oil was dissolved in ethyl acetate (10 mL), and this solution was passed through an alumina (basic) filter (approximately 100 g) followed by ethyl acetate (1,500 mL). The resulting filtrate was evaporated under reduced pressure to yield Compound 7j (0.44 g, 2.73 mmol, 27%) as a white solid: mp, 149.0°–151.0° C.; IR (KBr) 1,620, 1,590, 1,505, 1,475, 1,455, 1,410 cm$^{-1}$; $^1$H NMR (CDCl$_3$) 8.68 (br m, 1H), 7.47 (d, J=8.8 Hz, 1H), 7.21 (t, J=3.0 Hz, 1H), 6.50 (d, J=8.8 Hz, 1H), 6.49–6.47 (m, 1H), 3.10 (s, 6H); $^{13}$C NMR (CDCl$_3$) δ 156.6, 144.3, 126.4, 120.8, 102.7, 102.0, 39.3; LRMS (m/z, relative intensity) 162 (21), 161 (M+, 99), 160 (23), 146 (80), 132 (100), 119 (36), 118 (82), 117 (81), 90 (19). Anal. Calcd for C$_9$H$_{11}$N$_3$: C, 67.06; H, 6.88; N, 26.08; found: C, 66.69; H, 6.81; N, 25.94.

EXAMPLE 10

5-Methylpyrrolo[3,2-b]pyridine (Compound 7k)

To a stirred slurry of sodium hydride (60%) in oil, 18.2 g, 455 mmol, 2.0 eq) in anhydrous tetrahydrofuran (250 mL) under nitrogen at 0° C. was added dropwise a solution of di-t-butylmalonate (97.9 g, 453 mmol, 2.0 eq) in anhydrous tetrahydrofuran (150 mL). The mixture was allowed to warm to room temperature, and was then heated at 45° C. for 30 minutes. The reaction mixture was then cooled to room temperature and 2-chloro-5-nitropyridine (35.9 g, 226 mmol) was added as a solid all at once. The resulting mixture was heated at reflux (66° C.) under nitrogen for 2 hours. The reaction was then cooled, placed in separatory funnel, water (200 mL) was added, the pH was adjusted to 6 with 10% HCl, ethyl ether (200 mL) was added, and the organic layer was removed. The remaining aqueous layer was then extracted once with ethyl ether (200 mL), and the organic extracts were combined, dried (MgSO$_4$), and evaporated under reduced pressure. The resulting solid/oil mixture was stirred in ethyl ether/hexanes (1:1, 300 mL) and the undissolved solid was filtered to yield t-butyl (2-t-butoxycarbonyl)-(5-nitro-2-pyridyl) acetate (46.0 g, 135 mmol, 60%) as a white, crystalline solid: mp, 105–106° C.; IR (KBr) 1,740, 1,730, 1,600, 1,575, 1,520, 1,460, 1,390, 1,370, 1,365, 1,330, 1,310 cm$^{-1}$; $^1$H NMR (CDCl$_3$) δ 9.36 (d, J=2.6 Hz, 1H), 8.48 (dd, J=2.6 and 8.7 Hz, 1H), 7.75 (d, J=8.6 Hz, 1H), 4.89 (s, 1H), 1.47 (s, 18H); LRMS (m/z, relative intensity) 227 (11), 209 (49), 182 (52), 164 (33), 57 (100); Anal. calc'd for C$_{16}$H$_{22}$N$_2$O$_6$: C, 56.80; H, 6.55; N, 8.28; found: C, 56.72; H, 6.57; N, 8.14.

To a stirred solution of potassium t-butoxide (11.0 g, 97.6 mmol, 3.3 eq) in anhydrous tetrahydrofuran (100 mL) at −10° C. under nitrogen was added dropwise a solution of (4-chlorophenoxy)acetonitrile (5.45 g, 32.5 mmol, 1.1 eq) and t-butyl (2-t-butoxycarbonyl)-(5-nitro-2-pyridyl)acetate (10.0 g, 29.6 mmol) in anhydrous tetrahydrofuran (75 mL). The resulting deep purple colored reaction was stirred at room temperature under nitrogen for 64 hours. 5% HCl (72 mL) was added to the reaction solution, and the resulting aqueous mixture was extracted with ethyl acetate (3×200 mL). These extracts were combined, dried (MgSO$_4$), and evaporated under reduced pressure to yield an oil. Column chromatography of this oil using silica gel (approximately 300 g) and elution with an ethyl ether/hexanes gradient (10–40% ethyl ether in hexanes) afforded (3-nitro-6-(dicarbo-t-butoxymethyl)-2-pyridyl)acetonitrile (5.14 g, 13.6 mmol, 46%) as a clear, pale yellow oil; IR (CHCl$_3$) 3,670, 2,970, 2,925, 2,255, 1,725, 1,600, 1,580, 1,520, 1,450, 1,395, 1,370, 1,350, 1,320 cm$^{-1}$; $^1$H NMR (CDCl$_3$) δ 8.49 (d, J=8.6 Hz, 1H), 7.81 (d, J=8.6 Hz, 1H), 4.92 (s, 1H), 4.40 (s, 2H), 1.48 (s, 18H); $^{13}$C NMR (CDCl$_3$) δ 165.4, 158.8, 145.0, 143.4, 133.9, 125.0, 115.1, 83.5, 62.3, 27.9, 26.8; LRMS (M/z, relative intensity) 322 (3), 265 (19), 248 (24), 221 (75), 204 (23), 203, (47), 57 (100); HRMS calcd. for C$_{18}$H$_{24}$N$_3$O$_6$ ([M+]+H): 378.1665, found: 378.1637; Anal. calc'd for : C$_{18}$H$_{23}$N$_3$O$_6$: C, 57.29; H, 6.14; N, 11.13; found: C, 56.96; H, 6.10; N, 10.97.

A mixture of (3-nitro-6-(dicarbo-t-butoxymethyl)-2-pyridyl)acetonitrile (6.85 g, 18.2 mmol), dioxane (150 mL), and 2M sulfuric acid (25 mL) was heated at reflux for 12 hours. The resulting solution was cooled, neutralized with sodium carbonate, and extracted with ethyl acetate (3×50 mL). These extracts were combined, dried (MgSO$_4$), and evaporated under reduced pressure to yield an oil. This oil was passed through a silica gel filter (approximately 100 g) followed by methylene chloride. This filtrate was evaporated under reduced pressure to afford (6-methyl-3-nitro-2-pyridyl)acetonitrile (1.91 g, 10.8 mmol, 59%) as an off-white solid: mp, 70°–72° C.; IR (KBr) 2,245, 1,595, 1,580, 1,515, 1,450, 1,370, 1,340 cm$^{-1}$; $^1$H NMR (CDCl$_3$) δ 8.38 (d, J=8.4 Hz, 1H), 7.37 (d, J=8.4 Hz, 1H), 4.39 (s, 2H), 2.70 (s, 3H); $^{13}$C NMR (CDCl$_3$) δ 164.7, 145.3, 142.1, 133.8, 123.9, 115.1, 27.1, 24.7; LRMS (m/z, relative intensity) 178 (29), 177 (M+, 93), 160 (16), 132 (26), 131 (92), 105 (37), 104 (100), 92 (32), 79 (50), 78 (51), 77 (81), 63 (54); HRMS 3.98; N, 23.72; found: C, 53.90; H, 3.95; N, 23.47.

A mixture of (6-methyl-3-nitro-2-pyridyl)acetonitrile (1.83 g, 10.3 mmol), Raney nickel (0.20 g) and acetic acid/ethanol (3:7) was shaken under an atmosphere of hydrogen for 4 hours. The resulting mixture was filtered, and the filtrate was evaporated under reduced pressure. The residual oil was partitioned between saturated sodium hydrogen carbonate (25 mL) and ethyl acetate (25 mL). The organic layer was removed, and the aqueous layer was extracted with ethyl acetate (2×25 mL). The organic extracts were combined, dried (MgSO$_4$), and evaporated under reduced pressure to yield a yellow solid. Column chromatography of this solid using silica gel (approx 50 g) and elution with 5% methanol in methylene chloride yielded Compound 7k (0.32 g, 2.4 mmol, 24%) as a tan solid: mp, 200°–202° C.; IR (KBr) 1,610, 1,570, 1,465, 1,445, 1,405, 1,290 cm$^{-1}$; $^1$H NMR (DMSO-d$_6$) δ 11.15 (br s, 1H), 7.65 (d, J=8.5 Hz, 1H), 7.54 (m, 1H), 6.95 (d, J=8.5 Hz, 1H), 6.45 (br m, 1H), 2.51 (s, 3H); $^{13}$C NMR (DMSO-d$_6$) 150.0, 145.7, 128.5, 126.6, 118.7, 116.0, 101.1, 24.2; Anal. calc'd for $C_8H_8N_2$; C, 72.70; H, 6:10; N, 21.20; found: C, 72.22; H, 6.19; N, 21.25.

EXAMPLE 11

5-Chloropyrrolo[2,3-c]pyridine (Compound 8)

A mixture of 200 mg Raney nickel (washed thoroughly with absolute ethanol), Compound 6 (2.35 g, 11.89 mmol), and 1:1 absolute ethanol/acetic acid (50 ml) was shaken under a hydrogen atmosphere (3 atm) for 2 hours. The reaction mixture was filtered, and the filtrate was evaporated under reduced pressure. The residual oil was placed in a saturated solution of sodium bicarbonate (25 ml), and this aqueous mixture was extracted with methylene chloride (3×25 ml). These extracts were combined, dried (MgSO$_4$), and evaporated under reduced pressure. The residual solid was stirred in cold anhydrous ether, and the undissolved solid was filtered to yield Compound 8 (0.80 g, 5.24 mmol, 44%) as a white crystalline solid: mp. 192°–194° C.; IR (KBr) 3,400, 3,080–2,750, 1,610, 1,565, 1,495, 1,455, 1,290 cm$^{-1}$; $^1$H NMR (CDCl$_3$) δ 9.55 (br s, 1H), 8.59 (s, 1H), 7.56 (s, 1H), 7.48 (t, J=2.8 Hz, 1H), 6.53–6.51 (m, 1H); $^{13}$C NMR (DMSO-d$_6$) δ 138.8, 135.4, 133.6, 132.6, 132.0, 113.8, 100.5; LRMS (m/z, relative intensity) 154 (34), 153 (13), 152 (M+, 100), 117 (68), 90 (19), 63 (14); HRMS calculated for $C_7H_5ClN_2$: 152.0136.

EXAMPLE 12

5-Methoxypyrrolo[2,3-c]pyridine (Compound 9)

A mixture of 4-methyl-5-nitro-1H-pyridine-2-one (5.00 g, 32.44 mmol), thionyl chloride (20 ml), and two drops of dimethylformamide was heated at reflux under nitrogen for 52 hours. The resultant orange colored solution was evaporated under reduced pressure, and a small amount of anhydrous toluene was added and then removed via evaporation under reduced pressure to remove traces of thionyl chloride. The residual oil then passed through a silica gel filter (dried at 150° C. under vacuum overnight, approximately 100 g) followed by methylene chloride (1 1). This filtrate was evaporated under reduced pressure to afford 2-chloro-4-methyl-5-nitropyridine (5.30 g, 30.71 mmol, 95%) as an orange oil, which crystallized below 0° C.; IR (CHCl$_3$) 1,605, 1,550, 1,520, 1,450, 1,360, 1,345 cm$^{-1}$; $^1$H NMR (CDCl$_3$) δ 9.03 (s, 1H), 7.83 (s, 1H), 2.60 (s, 3H); LRMS (m/z, relative intensity) 174 (25), 173 (19), 172 (M+, 68), 157 (74), 155 (100), 128 (27), 101 (47), 100 (55), 99 (74), 90 (43), 75 (36).

To a stirred solution of sodium (2.30 g, 100 mmol, 3.8 eq) in absolute methanol (75 ml) at 0° C., a solution of 2-chloro-4-methyl-5-nitropyridine (4.50 g, 26.07 mmol) in absolute methanol (15 ml) was added dropwise rapidly. The resulting dark colored solution was stirred at room temperature for 30 minutes, and then it was concentrted to a solid via evaporation under reduced pressure. This solid was placed in water (25 ml), the pH of which was adjusted to 6 with concentrated HCl, and this aqueous mixture was extracted with ethyl acetate (2×25 ml). These extracts were combined, dried (MgSO$_4$), and evaporated under reduced pressure to yield 2-methoxy-4-methyl-5-nitropyridine (4.30 g, 25.57 mmol, 98%) as an orange solid: mp, 70°–72° C.; $^1$H NMR (DMSO-d$_6$) δ 8.94 (s, 1H), 6.97 (s, 1H), 3.99 (s, 3H), 2.58 (s, 3H); LRMS (m/z relative intensity) 168 (M+, 98), 167 (100), 151 (34), 138 (24), 80 (17).

A solution of 2-methoxy-4-methyl-5-nitropyridine (4.30 g, 25.57 mmol) and dimethylformamide dimethylacetal (35 ml) was heated at reflux under nitrogen for 40 hours. Ethyl acetate was added to this solution (150 ml), and this mixture was washed with water (150 ml). The aqueous extract was back-extracted with ethyl acetate (100 ml), and the organic extracts were combined, dried (Na$_2$O$_4$), and evaporated under reduced pressure to yield a purple solid. The solid was dissolved in absolute ethanol (200 ml), and 5% palladium on carbon (3.0 g) was added to this solution which was shaken under a hydrogen atmosphere (3 atm) for 3 hours. The resultant reaction mixture was filtered, and the filtrate was evaporated under reduced pressure. Flash chromatography of the residue yielded compound 9 (2.05 g, 13.84 mmol, 54% last step, 50% overall) as a white crystalline solid: mp, 123°–124° C.; IR (KBr) 1,625, 1,580, 1,490, 1,460, 1,320, 1,150 cm$^{-1}$; $^1$H NMR (DMSO-d$_6$) δ 11.28 (br s, 1H), 8.37 (s, 1H), 7.57 (t, J=2.8 Hz, 1H), 6.86 (s, 1H), 6.33 (br m, 1H), 3.82 (s, 3H); $^{13}$C NMR (DMSO-d$_6$) δ 157.2, 136.4, 131.5, 130.7, 130.0, 99.6, 96.8, 53.4; LRMS (m/z, relative intensity) 149 (20), 148 (M+, 98), 147 (100), 119 (46), 118 (79), 117 (26), 105 (31), 91 (15), 70 (16); HRMS calculated for $C_8H_8N_2O$: 0:148.0657, found: 148.0613.

EXAMPLE 13

Male CD-1 mice (17–19 g at arrival) which had acclimated to the animal facility for approximately 6 days were housed 8 to a box. The mice were weighed and control or a compound of the present invention (drug) was then administered morning and afternoon for two days with at least six hours between sessions. On the third morning, the animals were weighed. Each of compounds 1a–1m, 2 and 3a–3c demonstrated at least a 5 percent reduction in body weight (as compared to day 1 morning weight) of drug animals versus control animals at a dosage of 32 mg/kg.

I claim:

1. A compound according to claim 1 selected from
   a) 3-(1,2,5,6-tetrahydropyrid-4-yl)pyrrolo[3,2-b]pyridine;
   b) 5-methoxy-3-(1,2,5,6-tetrahydropyrid-4-yl)pyrrolo[3,2-b]pyridine;
   c) 5-ethoxy-3-(1,2,5,6-tetrahydropyrid-4-yl)pyrrolo[3,2-b]pyridine;
   d) 5-propoxy-3-(1,2,5,6-tetrahydropyrid-4-yl)pyrrolo[3,2-b]pyridine;
   e) 5-isopropoxy-3-(1,2,5,6-tetrahydropyrid-4-yl)pyrrolo[3,2-b]pyridine;
   f) 5-butoxy-3-(1,2,5,6-tetrahydropyrid-4-yl)pyrrolo[3,2-b]pyridine;
   g) 5-t-butoxy-3-(1,2,5,6-tetrahydropyrid-4-yl)pyrrolo[3,2-b]pyridine;
   h) 5-benzyloxy-3-(1,2,5,6-tetrahydropyrid-4-yl)pyrrolo[3,2-b]pyridine;
   i) 5-cyclopentoxy-3-(1,2,5,6-tetrahydropyrid-4-yl)pyrrolo[3,2-b]pyridine;
   j) 5-hydroxy-3-(1,2,5,6-tetrahydropyrid-4-yl)pyrrolo[3,2-b]pyridine;
   k) 5-chloro-3-(1,2,5,6-tetrahydropyrid-4-yl)pyrrolo[3,2-b]pyridine;
   l) 5-dimethylamino-3-(1,2,5,6-tetrahydropyrid-4-yl)pyrrolo[3,2-b]pyridine;
   m) 5-methyl-3-(1,2,5,6-tetrahydropyrid-4-yl)pyrrolo[3,2-b]pyridine;
   n) 3-(1,2,5,6-tetrahydropyrid-4-yl)pyrrolo[2,3-b]pyridine;
   o) 3-(1,2,5,6-tetrahydropyrid-4-yl)pyrrolo[2,3-c]pyridine;

p) 3-(1,2,5,6-tetrahydropyrid-4-yl)pyrrolo[2,3-c]pyridine;

q) 5-methoxy-3-(1,2,5,6-tetrahydropyrid-4-yl)pyrrolo[3,2-c]pyridine;

r) 5-chloro-3-(1,2,5,6-tetrahydropyrid-4-yl)pyrrolo[3,2-c]pyridine;

and pharmaceutically acceptable salts thereof.

2. A compound according to claim 1 selected from a) 5-propoxy-3-(1,2,5,6-tetrahydropyrid-4-yl)pyrrolo[3,2-b]pyridine;

b) 5-butoxy-3-(1,2,5,6-tetrahydropyrid-4-yl)pyrrolo[3,2-b]pyridine;

c) 5-cyclopentoxy-3-(1,2,5,6-tetrahydropyrid-4-yl)pyrrolo[3,2-b]pyridine; and d) 5-hydroxy-3-(1,2,5,6-tetrahydropyrid-4-yl)pyrrolo[3,2-b]pyridine;

adn pharmaceutically acceptable salts thereof.

* * * * *